(12) United States Patent
Fortems et al.

(10) Patent No.: US 8,740,811 B2
(45) Date of Patent: Jun. 3, 2014

(54) BIOPSY DEVICE

(75) Inventors: Yves Fortems, Schilde (BE); Sven Maenhout, Leuven (BE); Kris Motmans, Leuven (BE); Andrea Jahraus, Leuven (BE); Wanda Oprea, Leuven (BE)

(73) Assignee: Dokter Yves Fortems BVBA, Schilde (BE)

( * ) Notice: Subject to any disclaimer, the term of this patent is extended or adjusted under 35 U.S.C. 154(b) by 121 days.

(21) Appl. No.: 13/201,686

(22) PCT Filed: Feb. 11, 2010

(86) PCT No.: PCT/EP2010/051683
§ 371 (c)(1),
(2), (4) Date: Aug. 16, 2011

(87) PCT Pub. No.: WO2010/092100
PCT Pub. Date: Aug. 19, 2010

(65) Prior Publication Data
US 2011/0301498 A1    Dec. 8, 2011

(30) Foreign Application Priority Data
Feb. 16, 2009 (GB) .................................. 0902495.1
Mar. 16, 2009 (GB) .................................. 0904411.6

(51) Int. Cl.
*A61B 10/02* (2006.01)
*A61B 19/00* (2006.01)

(52) U.S. Cl.
CPC ........... *A61B 10/0233* (2013.01); *A61B 10/025* (2013.01); *A61B 2019/462* (2013.01)
USPC ......................................... 600/567; 600/566

(58) Field of Classification Search
USPC .................................................. 600/566, 567
See application file for complete search history.

(56) References Cited

U.S. PATENT DOCUMENTS 3,996,935 A * 12/1976 Banko ............................. 604/22
4,163,446 A *  8/1979 Jamshidi ....................... 600/567
(Continued)

FOREIGN PATENT DOCUMENTS

| GB | 2 042 902 A | 10/1980 |
| WO | 97/22299 A1 | 6/1997 |
| WO | 2007/149302 A2 | 12/2007 |

OTHER PUBLICATIONS

Search Report & Report on Patentability pertaining to International Application No. PCT/EP2010/051683 dated Jun. 1, 2011.

*Primary Examiner* — Sean Dougherty
*Assistant Examiner* — Michael C Stout
(74) *Attorney, Agent, or Firm* — Dinsmore & Shohl LLP

(57) ABSTRACT

This invention relates to a biopsy device consisting of an inner cannula (4) and an outer hollow tube (1), a handle (7) which may be removably attached to the outer hollow tube, a locking system to secure the inner cannula and/or the attenuator in the outer hollow tube, and characterized in that the tip of the outer hollow tube is ellipse shaped and extends beyond the inner cannula, the latter ending in a blunt edge. The blunted tip of the outer hollow tube together with the sharpened ending of the inner cannula determines the cutting edge of the device. In combination the distal ends of inner cannula and outer hollow tube determine the biopsy depth size and shape of the biopsy sample in a reproducible way. In one embodiment of the present invention, the length of the inner cannula can be controlled, allowing varying the aforementioned sample parameters as desired.

14 Claims, 11 Drawing Sheets

(56) References Cited

U.S. PATENT DOCUMENTS

| | | | |
|---|---|---|---|
| 4,689,040 A * | 8/1987 | Thompson | 604/22 |
| 4,850,354 A * | 7/1989 | McGurk-Burleson et al. | 606/170 |
| 5,320,110 A * | 6/1994 | Wang | 600/566 |
| 5,357,974 A * | 10/1994 | Baldridge | 600/567 |
| 5,409,013 A * | 4/1995 | Clement | 600/566 |
| 5,676,012 A * | 10/1997 | Ceriale | 72/294 |
| 5,741,287 A * | 4/1998 | Alden et al. | 606/170 |
| 5,823,970 A * | 10/1998 | Terwilliger | 600/564 |
| 6,171,325 B1 * | 1/2001 | Mauze et al. | 606/171 |
| 6,702,760 B2 * | 3/2004 | Krause et al. | 600/564 |
| 8,313,489 B2 * | 11/2012 | Adams et al. | 606/80 |
| 8,343,073 B2 * | 1/2013 | Miller | 600/567 |
| 2005/0059905 A1 * | 3/2005 | Boock et al. | 600/567 |
| 2007/0066987 A1 * | 3/2007 | Scanlan et al. | 606/184 |
| 2007/0179403 A1 * | 8/2007 | Heske et al. | 600/567 |
| 2007/0293788 A1 * | 12/2007 | Entrekin et al. | 600/564 |
| 2008/0039874 A1 * | 2/2008 | Catanese et al. | 606/142 |
| 2008/0039883 A1 * | 2/2008 | Nohilly | 606/180 |
| 2008/0119759 A1 * | 5/2008 | McLain | 600/567 |
| 2008/0154217 A1 * | 6/2008 | Carrez et al. | 604/272 |
| 2008/0228104 A1 * | 9/2008 | Uber et al. | 600/567 |
| 2008/0234715 A1 * | 9/2008 | Pesce et al. | 606/171 |
| 2009/0163770 A1 * | 6/2009 | Torrie et al. | 600/114 |

* cited by examiner

DETAIL B
SCALE 3.000

DETAIL A
SCALE 3.000

BIOPSY DEVICE

FIELD OF THE INVENTION

The present invention relates to biopsy sampling and in particular to a device for such sampling in hard tissue on e.g. humans or animals. The biopsy device as provided herein is more in particular for sampling cartilage tissue, such as at the non-weight bearing areas of the superomedial or superolateral edge of the femoral condyle or the lateral and medial intercondylar notch.

BACKGROUND TO THE INVENTION

Autologous chondrocyte implantation (ACI) is a clinically relevant treatment to repair articular cartilage in patients with knee cartilage defects. This repair method is based on the introduction of adult chondrogenic cells into the defect area. To accomplish this, chondrocytes are first isolated from a limited amount of articular cartilage harvested arthroscopically from a minor weight-bearing area of the injured knee of the same patient. The cells are released from the cartilage tissue by enzymatic digestions and expanded in culture medium until a sufficient number of cells are obtained to fill the focal cartilage defect. The most common sites for cartilage biopsy harvest recommended by orthopedic surgeons are the non-weight bearing areas of the superomedial or superolateral edge of the femoral condyle or the lateral and medial intercondylar notch. Today, an arthroscopic gouge or ring curette is used to obtain two or three small slivers of partial to full thickness cartilage. However, the harvested cartilage quantity is highly variable amongst surgeons due to device user characteristics.

The cartilage harvest procedure plays a crucial role in the process of cell cultivation, since sufficient starting material must be available to allow a successful manufacturing of the cells. On the other side, the biopsy amount taken must be restricted in order to minimize the lesion size created at the biopsy harvesting site. A controlled and consistent biopsy harvesting process is therefore highly desired.

Currently available biopsy devices are not designed to give consistent cartilage harvest material without contaminations by other tissues or the risk of loosing the biopsy during the procedure, or are restricted to only being used at specific sites (e.g. the notch).

One example of such a standard instrument is the Wiberg device as shown in FIG. 1. The device is a re-usable, stainless steel instrument with flat handle, long neck, and sharp-edged scoop at the end. The biopsy is taken by inserting the scoop into the cartilage, and then pushing and wiggling the instrument through the cartilage to obtain a biopsy piece. Biopsy quantities obtained with this instrument are extremely user dependent and lack standardization. Even with the same surgeon (user), a lack of consistent reproducibility has been observed despite long-term experience. Furthermore, the device is not user friendly since no control on the tissue depth and length is provided. In addition, it bears the risk of losing the biopsy during the arthroscopic procedure since the sample is not captured within the device. Consequently, one needs to use a slow, difficult "whittling" motion in order to obtain the cartilage sample.

Another example is the Storz instrument. The device uses a "punch" mechanism which punches out a small circular sample, comprising both a cartilage sample and part of an osteochondral layer. It is used at a perpendicular angle to the cartilage layer, punches through the entire layer, as well as the osteochondral layer—collecting the sample inside the instrument. This cartilage harvest device was specifically designed to obtain biopsies for the notch and can only be used at this location; and is used mainly in the German market. Only a small, limited amount of biopsy material can be harvested which often contains contaminating subchondral bone mass that is "punched out" together with the cartilage during sampling.

It is a particular object of the present invention to provide a biopsy device that addresses the aforementioned problems in that;
 it is applicable to all locations within the knee joint (arthroscopic accessibility) with in particular the lateral and medial intercondylar notch;
 it allows a controlled and consistent biopsy harvesting process;
 it gives consistent cartilage harvest material without contaminations by other tissues or the risk of loosing the biopsy during the procedure.

It is accordingly a general object of the invention to provide consistent biopsies, in width and height, without contamination by other tissues, that can be taken at all locations within the knee joint.

BRIEF DESCRIPTION OF THE DRAWINGS

With specific reference now to the figures in detail, it is stressed that the particulars shown are by way of example and for purposes of illustrative discussion of the different embodiments of the present invention only, and are presented in the cause of providing what is believed to be the most useful and readily description of the principles and conceptual aspects of the invention. In this regard no attempt is made to show structural details of the invention in more detail than is necessary for a fundamental understanding of the invention, the description taken with the drawings making apparent to those skilled in the art how the several forms of the invention may be embodied in practice.

DETAILED DESCRIPTION OF THE INVENTION

The biopsy device of the present invention solves the problems associated with the aforementioned prior art devices in that it provides:

1) the ability to control and select the biopsy length (shape and size) in relation to the defect size;
2) the ability to standardized biopsy harvesting at all locations in the knee joint, with in particular the lateral and medial intercondylar notch;
3) the ability to avoid osteochondral defects for reasons of patient safety and product contamination with non-chondrogenic cells;
4) a cartilage insertion into the biopsy needle with minimal tissue damage;
5) a capturing chamber for the biopsy sample to minimize risk of loss;
6) a measurable and visible positioning of the device;
7) a user-friendly and safe use;
8) a single-use to reduce the risk of contamination and/or infection and to maintain its sharpness.

Figure 6:
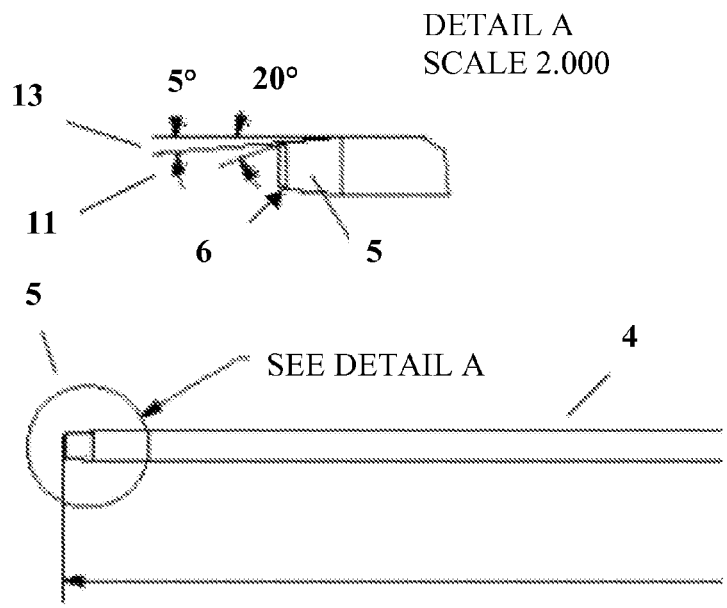
FIG. 6 shows an embodiment of the inner cannula according to the invention.

The invention relates to a biopsy device as shown in FIGS. 2a, 2b, 7, 8a, 8b, 9b, 12 and 13 comprising an inner cannula (4) and an outer hollow tube (1), a handle (7) which can be removably attached to the outer hollow tube, a locking system (14) to close the handle when in use and to secure the inner cannula or the attenuator (15), optionally having a handle (20), in the biopsy device, and characterized in that the tip (2) of the outer hollow tube is ellipse shaped and extends beyond the inner cannula (FIG. 3), the latter having a cutting edge (5), such as for example a truncated cone or truncated pyramid (FIG. 6). The biopsy device of the present invention is particularly well suited for Autologous Chondrocyte Implantation (ACI) treatment or any other biopsy scraping technique.

As such, the present invention provides a system for a biopsy device comprising an inner cannula having a cutting edge, such as a truncated cone or a truncated pyramid and an outer hollow tube extending beyond said inner cannula, said outer hollow tube having an ellipse shaped cutting edge.

As used herein, the inner cannula and outer hollow tube consist of needles that are typically made of metal, e.g. stainless steel or a non-ferrite metal. It is preferred that the inner cannula and outer hollow tube as a whole are provided out of stainless steel or other rust-free metal, e.g. medical grade stainless steel.

Figure 4:
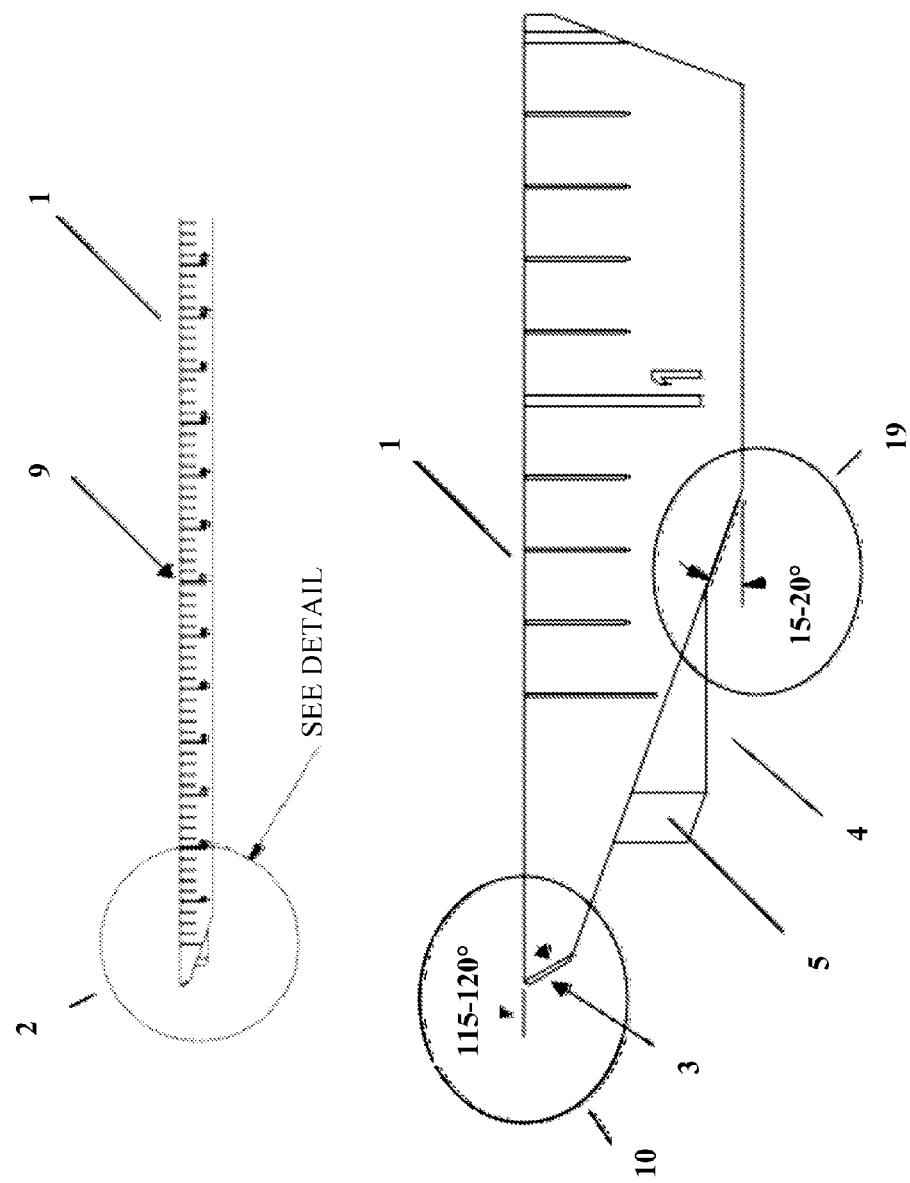
FIG. 4 shows an embodiment of the outer hollow tube according to the invention.

FIG. 4 shows an embodiment of the outer hollow tube according to the invention. The outer hollow tube (1) is between and about 15.0 to 20.0 cm long, in particular about 17.0 cm, measured between the tip of the outer hollow tube and the handle.

The outer hollow tube has an outer diameter of about and between 4.0-6.0 mm and in inner diameter of about and between 3.0-5.0 mm. In a particular example, the outer needle has an outer diameter of about 5.0 mm and in inner diameter of about 4.0 mm.

Figure 5:
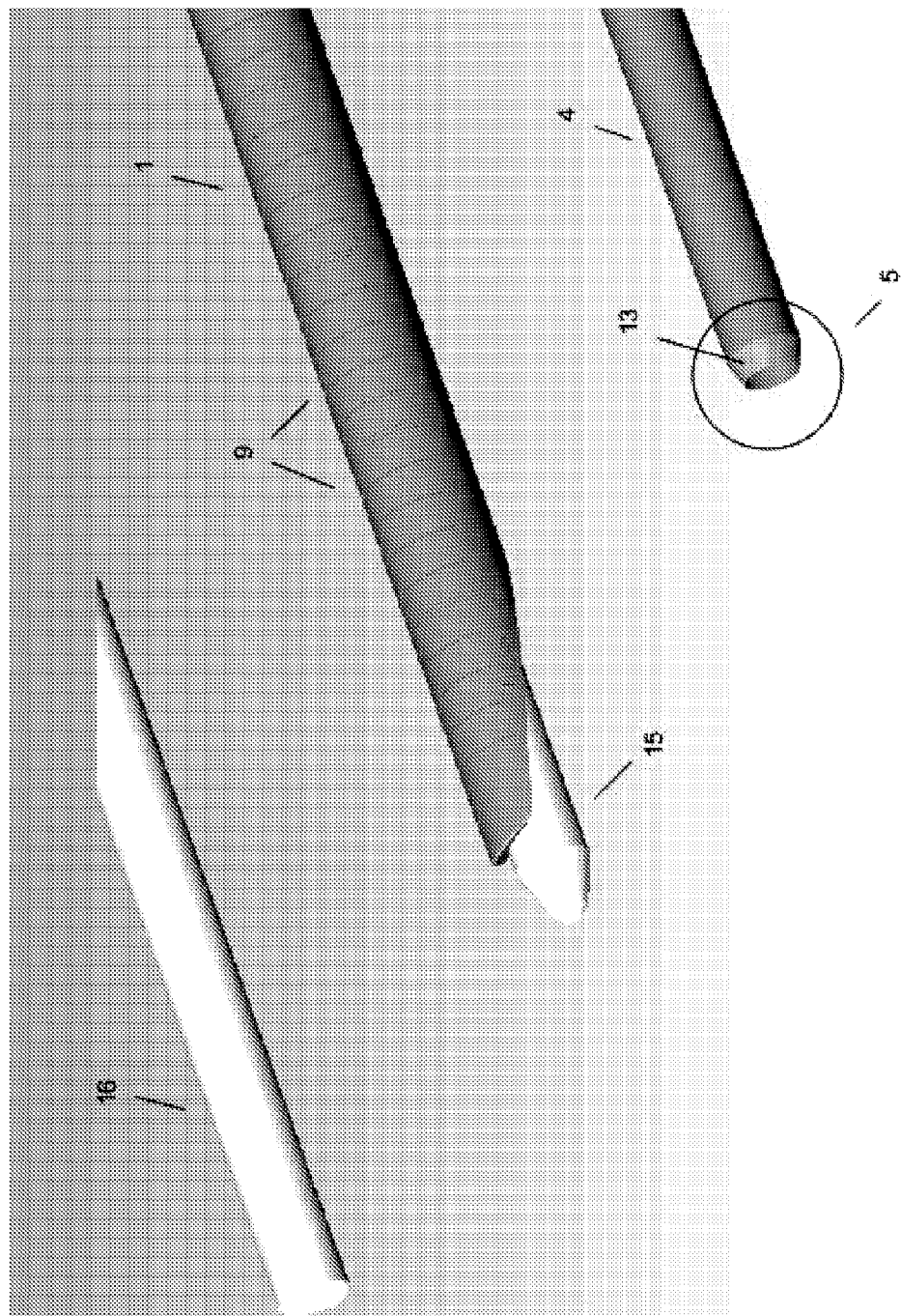
FIG. 5 shows a grading system (9) applied on the outer hollow tube (1). The attenuator (15) inserted into the outer hollow tube. The inner cannula (4) with the truncated cone tip (5) and the stick (16) device to remove the biopsy samples from the inner cannula.

Optionally the outer hollow tube comprises at the outer surface a grading system (9) to measure the advancement of the device during harvesting. In a particular embodiment a laser-marking is applied every 10 mm (FIG. 5).

The extended ellipse shaped tip (2) of the outer hollow tube (1) is further characterized in that it is blunt at the most distal end (3) and has a bevel angle of about 10-30°, in particular 15° or 20° (19). This tip (3) of the outer hollow tube, together with the sharpened edge (6) of the inner cannula will compose the cutting edge (3,5) of the device (See FIGS. 4 and 6).

As such, these elements will determine the biopsy depth, size and shape of the biopsy samples. The tip of the outer hollow tube assists in the correct positioning of the device at the site of harvesting. It is accordingly important that the tip of the outer hollow tube is shaped with high precision such that the outer beveled surface (10) has a higher angle than the inner surface at its distal end. The angle of the outer beveled surface is suitably 115° but may vary from about 100° to 120°, and is in particular 117°.

FIG. 6 shows an embodiment of the inner cannula (4) according to the invention. Like for the blunt tip of the outer hollow tube, the angle of the outer beveled surface (11) at the cutting edge of the inner cannula (needle) is suitably 20° but may vary from about 17 to 25°. The angle of the inner beveled surface (13) of the inner cannula (needle) is suitably 5°, but may vary from about 3 to 8°. As such the cone/pyramidal part of the inner cannula (needle) (13) has a bevel angle of about 3-8°, and is in particular 5°.

The position of the cutting edge of the inner cannula together with the tip of the outer hollow tube, determines the cutting depth of the biopsy device. When the tip (cutting edge) of the inner cannula is more retracted when compared to the tip of the outer hollow needle, the cutting depth will decrease. When the tip (cutting edge) of the inner cannula is more advanced, the cutting edge will increase.

Figure 10:
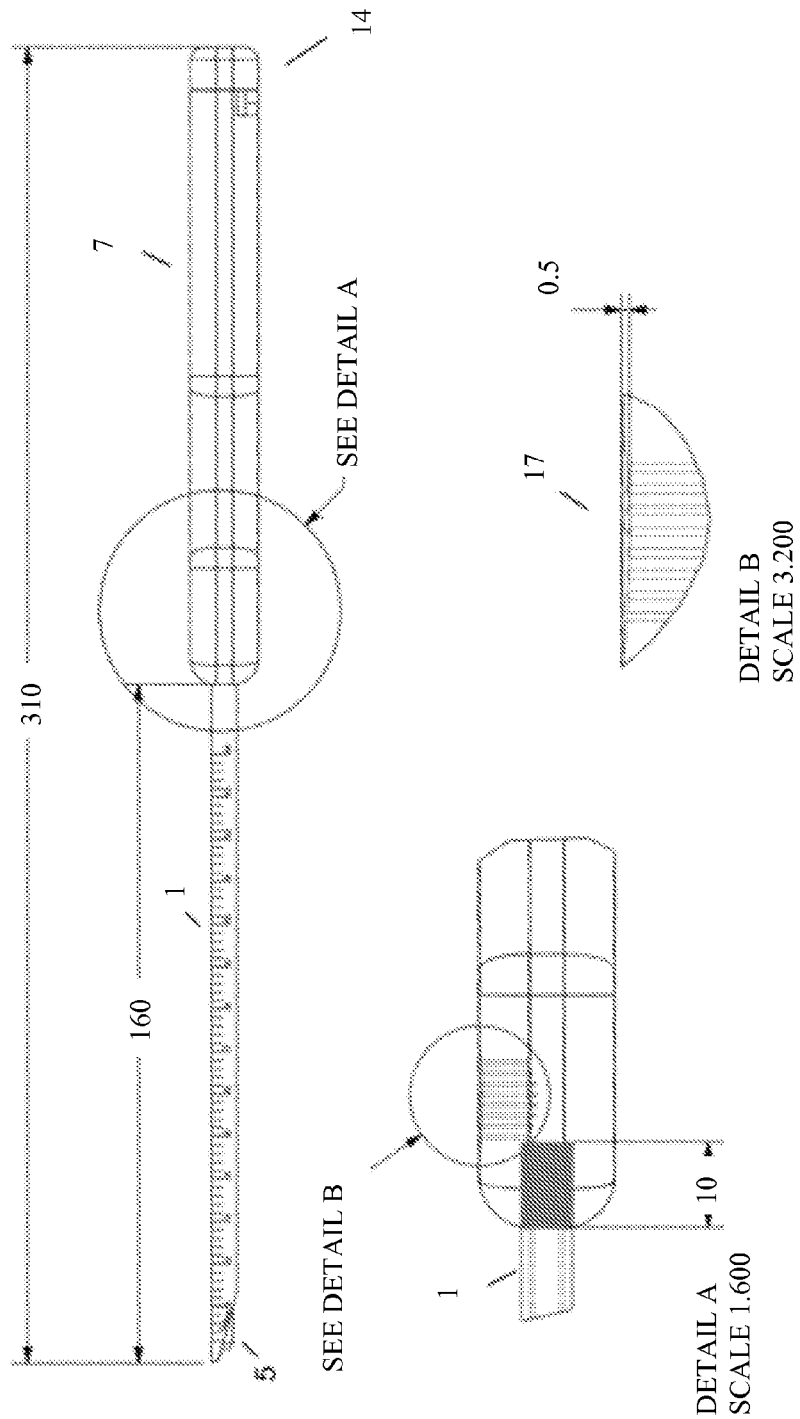
FIGS. 10 and 11 show embodiments of a biopsy device according to the invention providing a pressure release system (17) consisting of a perforated indentation in the handle (7) proximal of the inner cannula (4).
Figure 11:
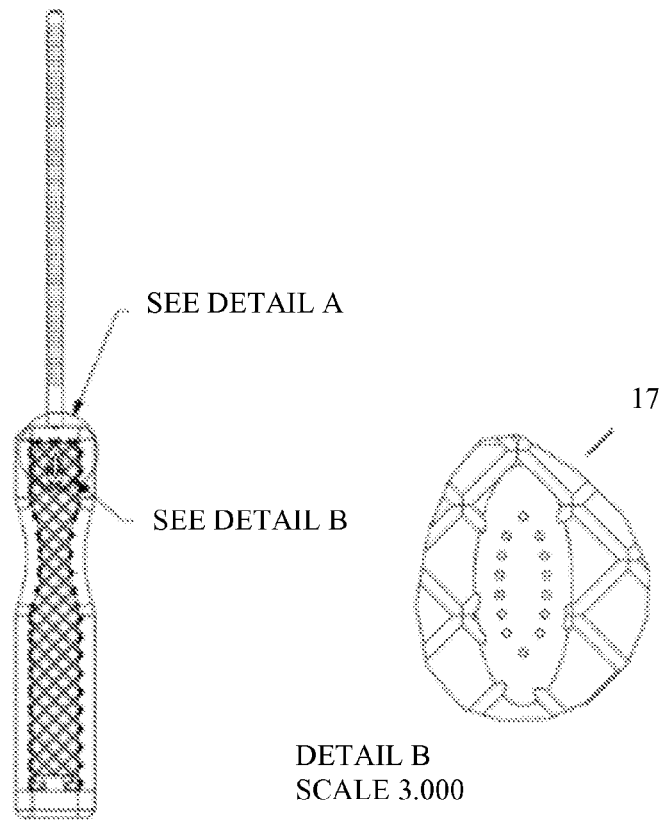
Figure 11:
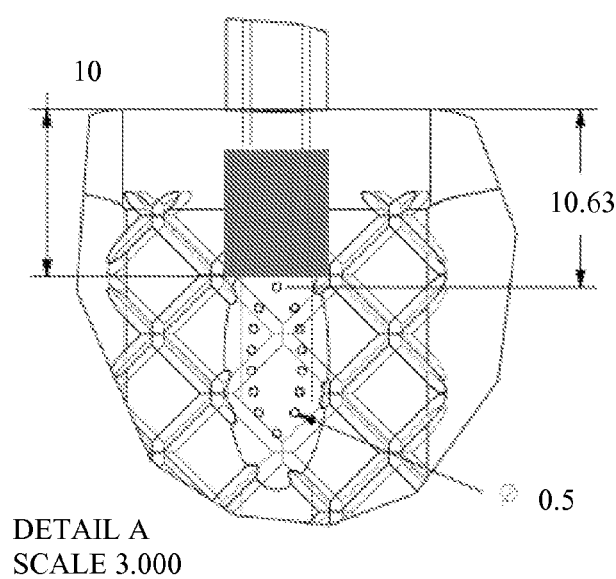
Figure 12:
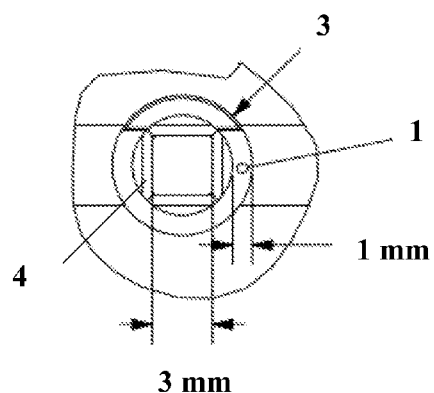
FIG. 12 shows the frontal view of the device wherein the inner cannula (needle) has a truncated pyramidal cutting edge.
Figure 13:
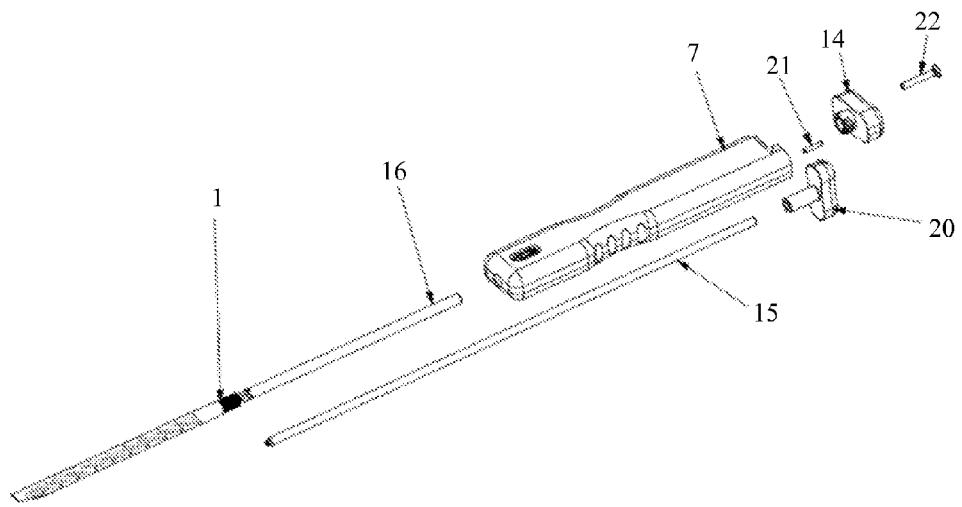
FIG. 13 shows an embodiment of a biopsy device according to the invention

In the particular ACI application of the present invention, the inner cannula is proximally fixed at between and about 3.0 to 5.0 mm from the most distal tip of the outer hollow needle, more in particular at about 3.4 or 4.0 mm. In said embodiment the cutting depth is between and about 2.0 to 2.5 mm; in particular about 2.4 mm thick. In one embodiment of the present invention, such as for example shown in FIGS. 7, 8a and 8b, 9a, 9b, 9c and 13, the back end of the device will have a locking system (14) for positioning and fixing the inner cannula and/or the attenuator (15) in respect to the outer hollow tube and to close the handle when in use. Depending on the design of the locking system, the device may further contain a fixation pin (21) and/or a screw (22) for positioning and/or attaching the locking system (14) onto the device, as shown in FIG. 13. Preferably, in this embodiment, and as for example shown in FIGS. 8b, 10 and 11, the inner cannula and outer hollow tube form an integrated part with one another, i.e. consist of a single piece.

Figure 7:
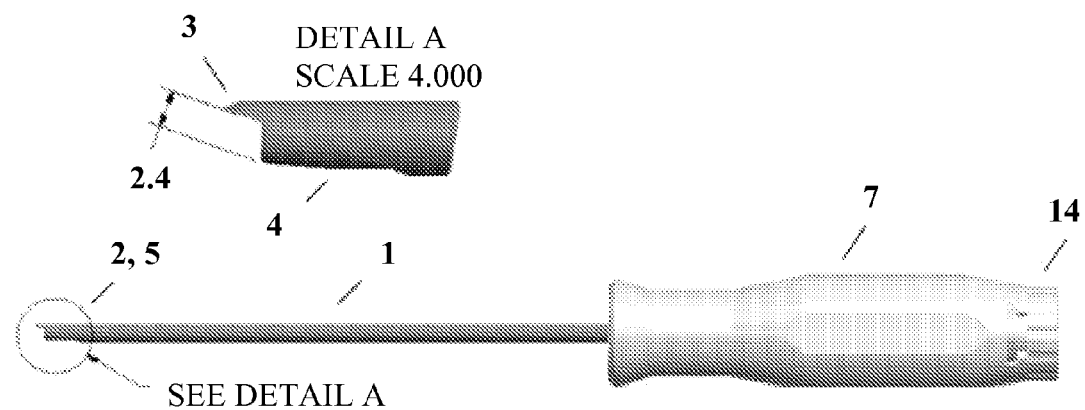
FIG. 7 illustrates the cutting depth of a biopsy device according to the invention.

In an alternative and further embodiment of the present invention the inner cannula is controllably positioned within the device, such that the length of the inner cannula within the outer hollow tube can be adjusted as desired but never extends beyond the most distal tip of the outer hollow tube. Through adjustment, such as for example by means of a turning knob, of the position of the tip of the inner cannula, the cutting depth can range between and about 1.0 to 4.0 mm, and is typically between and about 1.2 to 2.8 mm thick, in a particular embodiment 2.1 mm (FIG. 7).

The outer diameter of the inner cannula (needle) (4) should be such that it closely fits the inner surface of the outer hollow tube. It will accordingly range between and about 4.0 to 6.0 mm, and in particular has an outer diameter of about 4.0 mm. The inner diameter of the inner cannula (needle) ranges between and about 3.0 to 5.0 mm, and in particular has an inner diameter of about 3.0 mm.

Figure 8A:
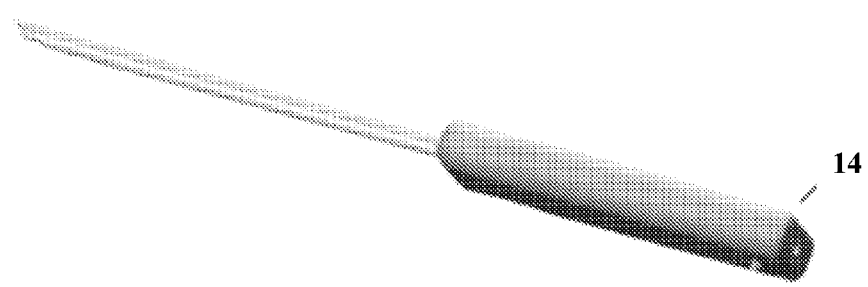
FIGS. 8a-c illustrates an embodiment of a biopsy device according to the invention providing a pressure release system (18) applied to the handle (a: opening; b,c: valve). A device to remove the samples from the inner cannula after harvesting (white needle with the truncated top (16)); an attenuator, having a handle (20) to close the system of the present invention when entering device into the body (the white needle with the sharpened top (15) alternatively the attenuator consists of a cap that closes the device when entering the device into the body, and which is retractable through the inner cannula).
Figure 8B:
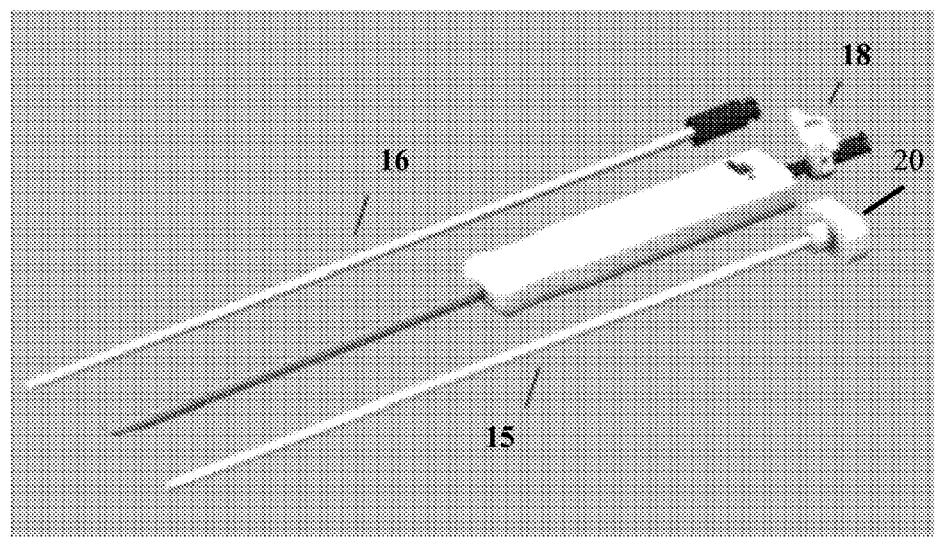
Figure 8C:
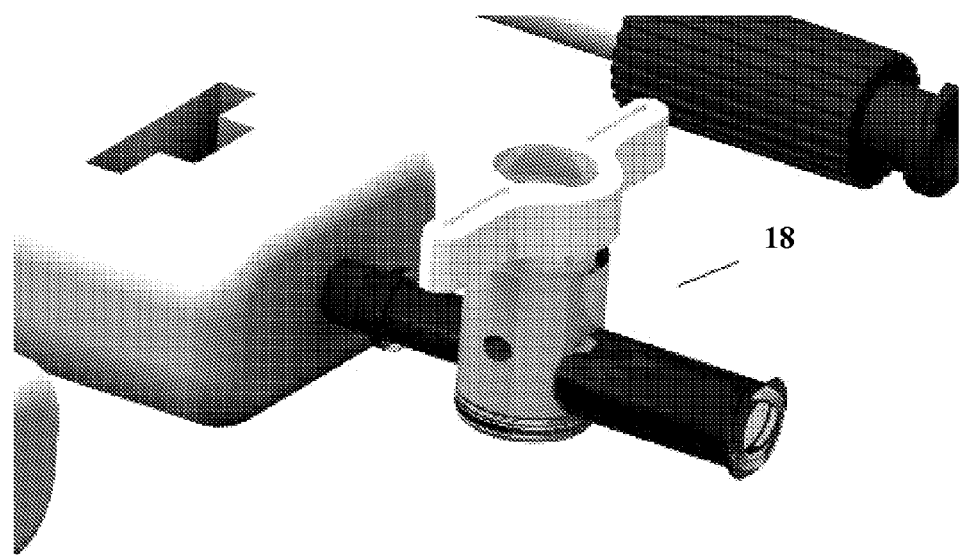
Figure 9A:
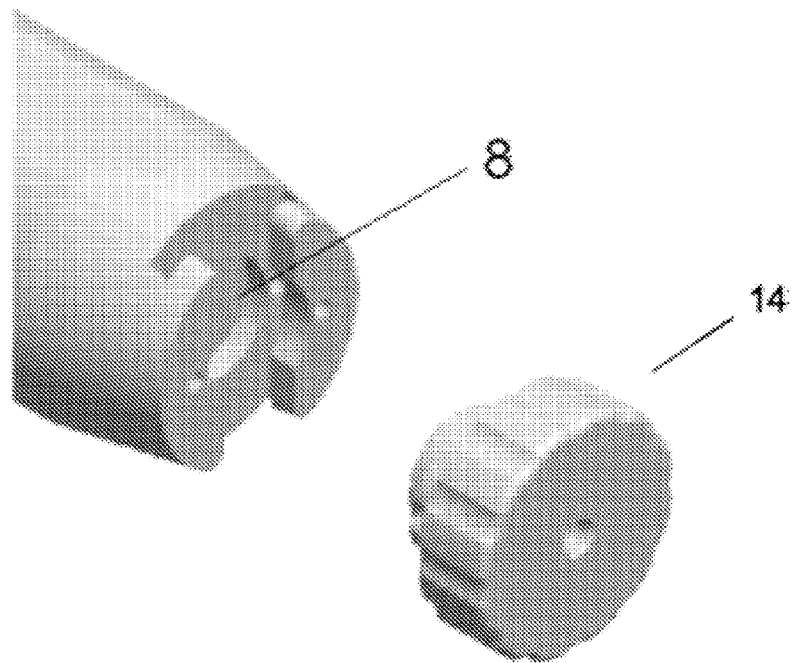
FIGS. 9a, 9b and 9c show embodiments of a locking system (14) for positioning the inner cannula and the outer hollow tube, and for closing the handle when in use.
Figure 9B:
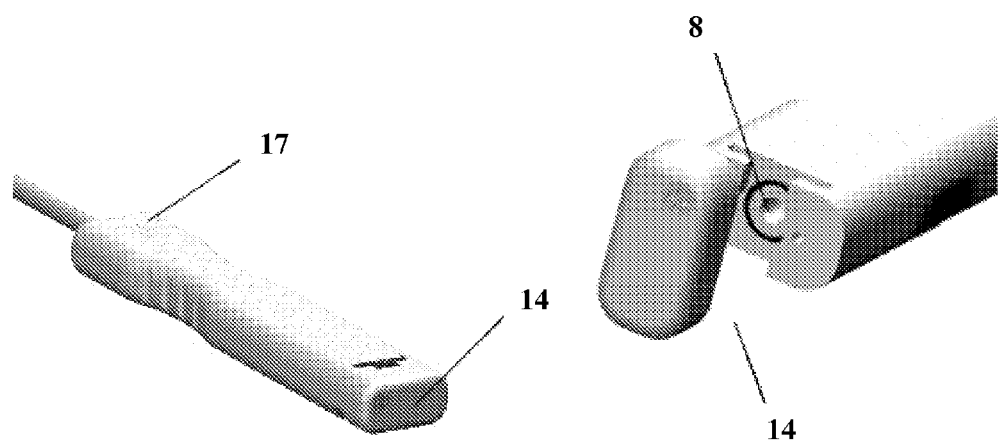
Figure 9C:
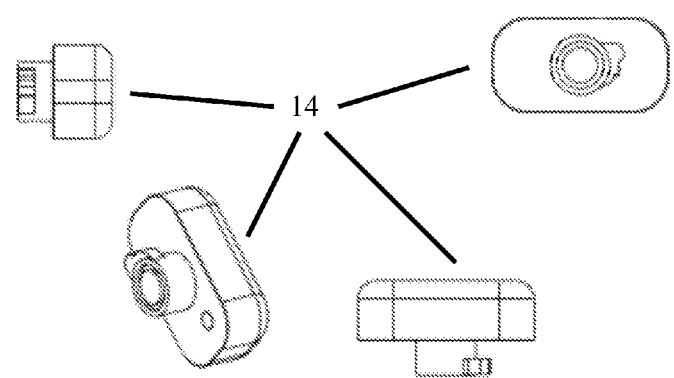

As the biopsy samples are captured inside the inner cannula (needle), an opening (8) (FIG. 9a, 9b) needs to be at the top of said cannula (needle) to allow pressure release (so that there is minimal pressure on the biopsy material in the tube) during the harvesting procedure, and to allow recovery of the collected samples after harvesting. This opening is typically an integrated part of the handle at the proximal end of the inner cannula (needle). In a particular embodiment the handle provides a valve for pressure release from the inner cannula (needle). FIG. 8b illustrates an embodiment of a biopsy device according to the invention providing a valve (18) applied to the handle (FIG. 8c for detail). In a further embodiment, the handle provides a perforated indentation (17) to control pressure release from the inner cannula (needle) with the fingertip of the manipulator.

At said back end of the device a locking system (14) is provided on the one hand and as explained hereinbefore, to secure the inner cannula (4) or attenuator (15) in the biopsy device when entering the device into the body; and on the other hand to close the handle when in use. Any art known locking system to lock a cannula in a tube can be used. Examples of an inner cannula knob that fits in the outer hollow tube handle, are provided in FIGS. 8a, 9a, 9b, 9c and 13.

Figure 1:
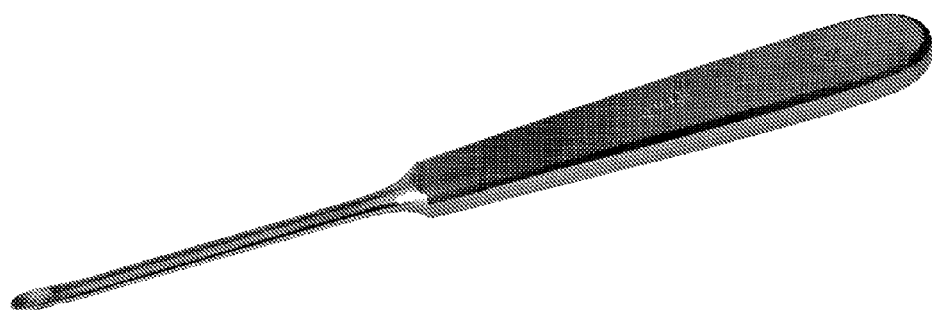
FIG. 1 shows a prior art biopsy device.
Figure 2A:
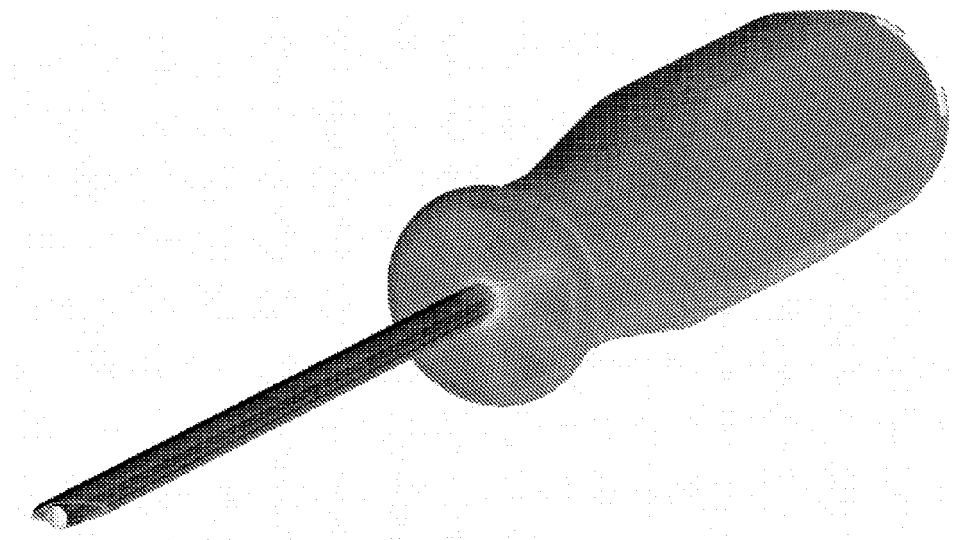
FIGS. 2a and 2b show embodiments of a biopsy device according to the invention.
Figure 2B:
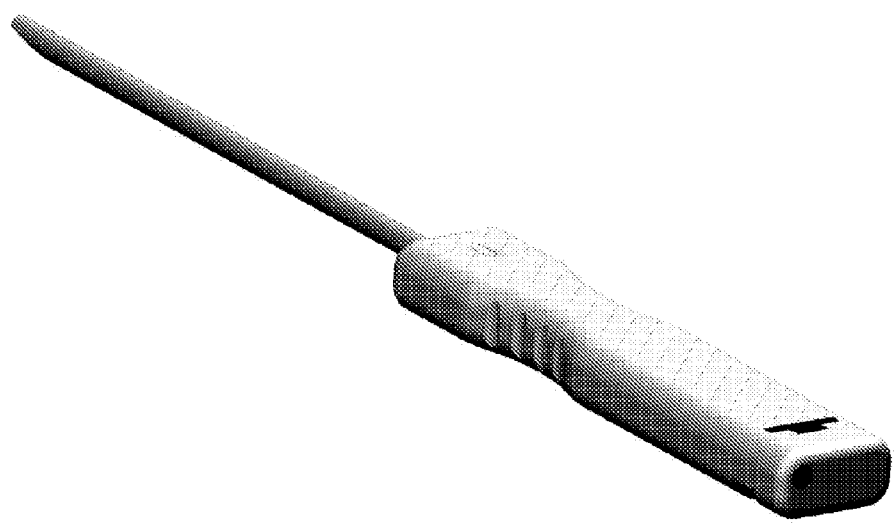
Figure 3:
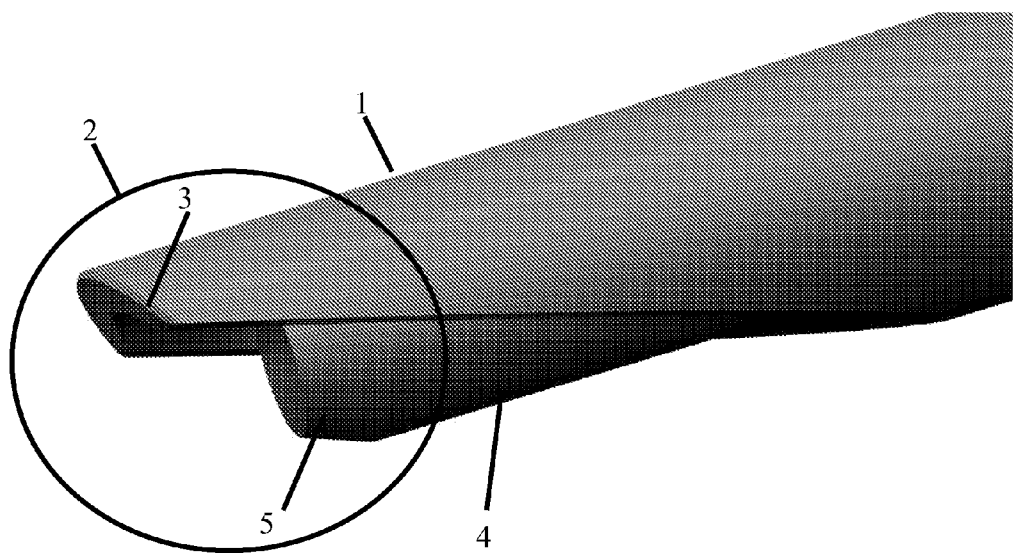
FIG. 3 shows a detail of the tip of the inner cannula (5) and the outer hollow tube (1) of a biopsy device according to the invention.

The handle (7) of the device is designed to fit ergonomically into the hand. In one embodiment, as shown in FIG. 2a, the round side is to be placed into the palm of the hand so that the flat sides are embraced with the fingers and the thumb. In another embodiment of FIG. 2b, the handle has a flatter shape, and may comprise a perforated indentation (17) to allow pressure release (so that there is minimal pressure on the biopsy material in the tube) during the harvesting procedure. The material should be such that it feels warm and comfortably in the hand. Also and preferably the material should be able to resist steam temperatures during sterilization. The sterilizable material is preferably made of a plastic material, for example a polycarbonate or a polyacetal such as ertacetal.

The present invention further provides a method for performing a biopsy, comprising the following steps:
a) Positioning an attenuator within or cap on the biopsy device of the present invention;
b) Entering the biopsy device into the body;
c) Positioning the tip of the biopsy device to the sampling surface;
d) Removing the attenuator or cap from the biopsy device and optionally replacing the attenuator with the inner cannula;
e) Sliding the tip of the outer hollow tube over the sampling surface to cut the biopsy sample with the tip of the inner cannula;
f) Harvesting the biopsy sample within the inner cannula, while releasing pressure from said inner cannula;
g) Retracting the biopsy device from the body; and
h) Opening the biopsy device at the back to push the biopsy samples out of the biopsy device.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

The invention claimed is:

1. A biopsy device comprising
an inner cannula having a cutting edge;
an outer hollow tube extending beyond said inner cannula and having an ellipse shaped cutting tip, wherein the extended ellipse shaped tip of the outer hollow tube is blunt at its most distal end; and
a handle removably attached to the outer hollow tube and comprising a pressure release system for the inner cannula, which includes a perforated indentation thereon configured to control pressure release from the inner cannula by a finger of a manipulator.

2. The device of claim 1 wherein the tip of the outer hollow tube, together with the tip of the inner cannula, composes the cutting edge of the biopsy device.

3. The device according to claim 1 wherein the extended ellipse shaped tip of the outer hollow tube forms a bevel angle of about 10-30°.

4. The device according to claim 3 wherein the tip of the outer hollow tube has an outer beveled surface which is shaped such that the angle of the outer beveled surface is from about 100° to 120°.

5. The device according to claim 4 wherein the angle of the outer beveled surface at the cutting edge of the inner cannula is from about 17 to 25°.

6. The device according to claim 1 wherein the outer hollow tube is about 15.0 to 20.0 cm long.

7. The device according to claim 1 wherein the outer hollow tube has an outer diameter of between about 4.0-6.0 mm and an inner diameter of between about 3.0-5.0 mm.

8. The device according to claim 7 wherein the outer diameter of the inner cannula closely fits the inner surface of the outer hollow tube.

9. The device according to claim 1 wherein the inner cannula is controllably positioned within the device such that the length of the inner cannula within the outer hollow tube is adjustable.

10. A biopsy device according to claim 1, further comprising a locking system to secure the inner cannula in the outer hollow tube.

11. The biopsy device according to claim 10, wherein the pressure release comprises a valve.

12. A method for gathering a biopsy sample comprising:
providing a biopsy device comprising
an inner cannula having a cutting edge;
an outer hollow tube extending beyond said inner cannula and having an ellipse shaped cutting tip, wherein the extended ellipse shaped tip of the outer hollow tube is blunt at its most distal end; and
a handle removably attached to the outer hollow tube and comprising a pressure release system for the inner cannula, which includes a perforated indentation thereon configured to control pressure release from the inner cannula by a finger of a manipulator;
closing the biopsy device; entering the biopsy device into a body;
positioning the tip of the biopsy device to the sampling surface;
opening the biopsy device;

sliding the tip of the outer hollow tube over the sampling surface to cut the biopsy sample with the tip of the inner cannula;

harvesting the biopsy sample within the inner cannula while releasing pressure from said inner cannula;

retracting the biopsy device from the body; and removing the biopsy sample from the device.

13. The method according to claim 12 wherein the biopsy device is closed by inserting an attenuator into the outer hollow tube.

14. The method according to claim 12 wherein the biopsy device is closed by positioning a cap over the outer hollow tube.

\* \* \* \* \*